US005580565A

United States Patent [19]
Tighe et al.

[11] Patent Number: 5,580,565
[45] Date of Patent: Dec. 3, 1996

[54] USE OF CYANOACRYLATE ADHESIVES FOR PROVIDING A PROTECTIVE BARRIER FILM FOR THE SKIN

[75] Inventors: Patrick J. Tighe, Littleton, Colo.; Richard J. Greff, Yorba Linda, Calif.; Michael M. Byram; Leonard V. Barley, both of Colorado Springs, Colo.

[73] Assignee: MedLogic Global Corporation, Colorado Springs, Colo.

[21] Appl. No.: 299,935

[22] Filed: Sep. 1, 1994

[51] Int. Cl.$^6$ ..................................... A61K 9/00
[52] U.S. Cl. ................... 424/400; 424/443; 424/445; 424/78.02; 424/78.05; 424/78.08
[58] Field of Search ............................ 424/400, 78.02, 424/78.05, 78.08, 443, 445

[56] References Cited

U.S. PATENT DOCUMENTS

| | | | |
|---|---|---|---|
| 2,804,073 | 8/1957 | Galliene et al. | 424/78.06 |
| 3,527,224 | 9/1970 | Rabinowitz | 606/214 |
| 3,591,676 | 7/1971 | Hawkins et al. | 424/78.06 |
| 3,667,472 | 6/1972 | Halpern | 606/214 |
| 3,722,599 | 3/1973 | Robertson et al. | 606/214 |
| 3,995,641 | 12/1976 | Kroenthal et al. | 606/214 |
| 4,035,334 | 7/1977 | Davydov et al. | 424/78.06 |
| 4,379,863 | 4/1983 | Snyder | 523/105 |
| 4,444,933 | 4/1984 | Columbus et al. | 524/292 |
| 4,650,826 | 3/1987 | Waniczek et al. | 524/730 |
| 4,958,748 | 9/1990 | Otake | 222/131 |
| 5,306,490 | 4/1994 | Barley | 424/78.02 |

OTHER PUBLICATIONS

Akers, William A., "Treating Friction Blisters With Alkyl–α–cyanoacrylates", Arch Dermatol, vol. 107, 544–547, Apr. 173.
Bhaskar, Surindar N. et al., "Healing of Skin Wounds with Butyl Cyanoacrylate", pp. 294–297, 1969, Journal of Dental Research, vol. 48, No. 2.
Dalvi, A. et al., "Non–suture Closure of Wound Using Cyanoacrlate", pp. 97–100, 1986, Journal of Postgraduate Medicine, vol. 32, No. 2.
Eiferman, Richard A. et al., "Antibacterial Effects of Cyanoacrylate Glue", pp. 958–960, Jun. 1983, Archives of Ophthalmology, vol. 101.
Ellis, David A. F. et al., "The Ideal Tissue Adhesive in Facial Plastic and Reconstructive Surgery", pp. 68–72, 1990, The Journal of Otolaryngology, vol. 19, No. 1.
Fung, Ramona Q. et al., "Use of Butyl–2–Cyanoacrylate in Rabbit Auricular Cartilage", pp. 459–464, Jul 1985, Archives of Otolaryngology, vol. 111.
Galil, K. A. et al., "The Healing of Hamster Skin Ulcers Treated with N–butyl–2–cyanoacrylate (Histoacyl blue)", Journal of Biomedical Marterials Research, vol. 18.
Harper, Marion C., "Stabilization of Osteochondral Fragments Using Limited Placement of Cyanoacrylate in Rabbits", pp. 272–276, Jun. 1988, Clinical Orthopaedics and Related Research 231.

Kamer, Frank M. et al., "Histoacryl: Its Use in Aesthetic Facial Plastic Surgery", pp. 193–197, Feb. 1989, Archives of Otolaryngology Head and Neck Surgery, vol. 115.
Kosko, Paul I., "Upper Lid Blepharoplasty: Skin Closure Achieved with Butyl–2–Cyanoacrylate", pp. 424–425, Jun. 1981, Ophthalmic Surgery, vol. 12.
Lehman, Ralph A. W. et al., "Toxicity of Alkyl 2–Cyanoacrylate: Bacterial Growth", pp. 447–450, Sep. 1966, Archives of Surgery, vol. 93.
Leonard, Fred et al., "Synthesis and Degradation of Poly-(alkyl–a–Cyanoacrylate)", pp. 259–272, 1966, Journal of Applied Polymer Science, vol. 10.
Makady, F. M. et al., "Effect of tissue adhesives and suture patterns on experimentally induced teat lacerations in lactating dairy cattle", pp. 1932–1934, Jun. 1991, JAVMA, Reports of Original Studies, vol. 198, No. 11.
Matsumoto, Teruo, "Bacteriology and Wound Healing", pp. 106–113, 1972, Chapter 3 in Tissue Adhesives in Surgery.
Matsumoto, Teruo, "Clinical Considerations and Applications of Bucrylate Tissue Adhesive", Chapter 1 in Tissue Adhesives in Surgery, pp. 226–237, 1972.
Matsumoto, Teruo, "Reactions of the Organism to Acrylate–Adhesives", pp. 436–444, 1972, Tissue Adhesives in Surgery.
Matsumoto, Teruo et al., "Tissue Adhesive and Wound Healing", pp. 266–271, Mar. 1969, Archives of Surgery, vol. 98.
Mizrahi, S. et al., "Use of Tissue Adhesives in the Repair of Lacerations in Children", pp. 312–313, Apr. 1988, Journal of Pediatric Surgery, vol. 23, No. 4.
Morton, R. J. et al., "The Use of Histoacryl Tissue Adhesive for the Primary Closure of Scalp Wounds", pp. 110–112, 1988, Archives of Emergency Medicine, vol. 5.
Ousterhout, D. K. et al., "Cutaneous Adsorption of n–Alkyl–a–cyanoacrylate", pp. 157–163, 1968, Journal of Biomedical Materials Research, vol. 2.
Pepper, D. C., "Kinetics and Mechanism of Zwitterionic Polymerization of Alkyl Cyanoacrylate", pp. 629–637, 1980, Polymer Journal, vol. 12, No. 9.
Pepper, Davd Charles et al., "Kinetics of Polymerization of Alkyl cyanoacrylate by Tertiary Amines and Phosphines", pp. 395–410, 1983, Makromol. Chem., vol. 184.
Ronis, Max L. et al., "Review of Cyanoacrylate Tissue Glues with Emphasis of Their Otorhinolaryngological Applications", pp. 210–213, Feb. 1984, Laryngoscope., vol. 94.

(List continued on next page.)

*Primary Examiner*—Thurman K. Page
*Assistant Examiner*—William E. Benston, Sr.
*Attorney, Agent, or Firm*—Burns, Doane, Swecker & Mathis, L.L.P.

[57] ABSTRACT

A cyanoacrylate adhesive is applied onto skin area prone to exposure to discharge by patients suffering from incontinence so as to shield the skin from direct contact with the discharge. The adhesive can also be applied over medicament that has been applied onto skin surface and onto skin along the periphery of a stoma.

19 Claims, No Drawings

OTHER PUBLICATIONS

Saches, Michael Evan., "Enbucrylate as cartilage Adhesive in Augmentation Rhinoplasty", pp. 389–393, Jun. 1985, Archives of Otolaryngology, vol. 111.

Toriumi, Dean M. et al., "Histotoxicity of Cyanoacrylate Tissue Adhesives: A Comparative Study", pp. 546—550, Jun. 1990, Archives of Otolaryngology Head and Neck Surgery, vol. 116.

Tseng, Yin–Chao et al., "Modification of Synthesis and Investigation of Properties for 2-cyanoacrylate", pp. 73–79, Jan. 1990, Biomaterials, vol. 11.

Vinters, H. V. et al., "The Histotoxicity of Cyanoacrylate: A Selective Review", pp. 279–291, 1985, Neuroradiology, vol. 27.

Watson, David P., "Use of Cyanoacrylate Tissue Adhesive for Closing Facial Lacerations in Children", p. 1014, Oct. 1989, British Medical Journal, vol. 299.

USE OF CYANOACRYLATE ADHESIVES FOR PROVIDING A PROTECTIVE BARRIER FILM FOR THE SKIN

BACKGROUND OF THE INVENTION

1. Field of the Invention

This invention is directed to methods of forming a protective barrier layer on skin that is exposed to urine or fecal waste and is particularly suited for individuals suffering from incontinence, by use of a cyanoacrylate adhesive. The cyanoacrylate adhesive to be used can be stored in dispensers for single or repeated/intermittent use and can be applied to the skin by spraying, painting, etc. of the adhesive.

2. State of the Art

Cyanoacrylate adhesives have been suggested for a variety of adhesive purposes including glues and surgical adhesives. In particular, cyanoacrylate adhesives of formula I:

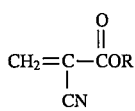

wherein R is an alkyl or other suitable substituents are disclosed in U.S. Pat. Nos. 3,527,224; 3,591,676; 3,667,472; 3,995,641; 4,035,334; and 4,650,826. Typically, when used as adhesives for living tissues, the R substituent is alkyl of from 2 to 6 carbon atoms and most often is butyl (e.g., n-butyl).

The suggested medical uses for cyanoacrylate adhesives include surgical environments wherein the cyanoacrylate adhesives are utilized, e.g., as an alternative to sutures or as a hemostat. Other suggested uses for these adhesives include their use in inhibiting blister and pressure ulcer formation, as described in U.S. Pat. No. 5,306,490, and U.S. patent application Ser. No. 08/082,927.

This invention is directed to the discovery that cyanoacrylates can be used to form in situ a protective barrier layer or coating over skin, including intact skin, to inhibit long term adverse effects of skin exposure to urine and/or fecal matter commonly encountered in patients suffering from incontinence.

In contrast to the methods of this invention, Snyder U.S. Pat. No. 4,379,863 describes the use of a composition to form a protective barrier film on skin. The composition comprises polymerized materials in the form of acrylate resins that are applied to the skin; the protective barrier firm is formed upon evaporation of the solvent. The protective barrier film so formed, however, has a variety of deficiencies associated with the use of prepolymerized films including weak adherence of the film to the skin and the inability to produce a film having a contour that closely matches the contour of the skin on which the film is applied.

SUMMARY OF THE INVENTION

This invention is drawn to methods for preventing infections and/or skin irritation by shielding skin, which can include intact skin, that is prone to exposure to microorganisms and other deleterious agents, with a protective barrier layer that is derived by polymerizing a cyanoacrylate adhesive to form an adhesive polymer coating. The inventive technique prevents the protected skin from the deleterious conditions associated with exposure to moisture and contaminants which otherwise would also be exacerbated by friction on the affected skin caused by contact with other skin and/or clothing. Further, the technique prevents skin break down caused by irritating body fluids which include, for example, discharge, perspiration and digestive juices from a stoma. The methods involve applying cyanoacrylate adhesive, particularly n-butyl cyanoacrylate adhesive, onto skin areas to form a flexible, waterproof, gas (e.g., $CO_2$ and $O_2$) permeable polymer layer over the skin areas. In turn, this polymer layer increases skin integrity while reducing the risk of infection by microorganisms. The method is particularly suited for individuals who suffer from incontinence or who require the use of ostomy appliances.

Accordingly, in one of its method aspects, this invention is directed to a method for shielding a patient's skin from discharge caused by incontinence, which method comprises:

applying to a surface skin area prone to exposure to said discharge a sufficient amount of a cyanoacrylate adhesive so as to cover said area; and polymerizing the cyanoacrylate adhesive so as to form a flexible, waterproof, adhesive polymer coating which adheres to the area where the adhesive was applied, wherein the cyanoacrylate, in monomeric form, is represented by formula I:

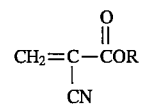

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

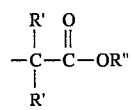

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

In another aspect, the invention is directed to methods of providing a protective covering over a medicament that has been applied onto skin or for skin along the periphery of a stoma which methods comprise applying the cyanoacrylate adhesive onto the medicament or skin and polymerizing said adhesive.

Preferably R is alkyl of from 2 to 10 carbon atoms and more preferably alkyl of from 2 to 8 carbon atoms. Even more preferably, R is butyl, pentyl or octyl and most preferably, R is n-butyl or iso-butyl.

In a preferred embodiment, the amount of cyanoacrylate applied is at least 0.02 milliliter (ml), and preferably from about 0.02 to about 0.3 ml, of cyanoacrylate adhesive per square centimeter of skin which is to be covered.

In another preferred embodiment, the cyanoacrylate adhesive to be applied to the skin has a viscosity of from greater than 2 to about 3000 centipoise at 20° C. More preferably, the cyanoacrylate adhesive is in monomeric form and has a viscosity of from greater than 2 to about 100 centipoise at 20° C. It is contemplated that pastes and gels having viscosities of up to 50,000 centipoise at 20° C. can also be employed.

The term "cyanoacrylate adhesive" refers to adhesive formulations comprising cyanoacrylate monomers of formula I:

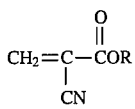

where R is selected from the group consisting of alkyl of 2 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

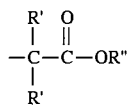

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl or iso-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Preferred cyanoacrylate adhesives for use in the invention are n-butyl-2-cyanoacrylate and iso-butyl-2-cyanoacrylate.

The cyanoacrylate adhesives described herein rapidly polymerize in the presence of water vapor or tissue protein, and the n-butyl-cyanoacrylate is capable of bonding to human skin tissue without causing histoxicity or cytotoxicity.

DETAILED DESCRIPTION OF THE PREFERRED EMBODIMENTS

This invention relates to cyanoacrylate adhesives which are used to form a protective barrier layer on skin, including more preferably, intact skin. (As used herein, the term "skin" can include either intact skin or broken down skin, or both, wherein the broken down skin is caused, for example, by moisture, friction, maceration, disease, ostomy devices, or combinations thereof.) The cyanoacrylate adhesive which is applied to the skin can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The cyanoacrylate adhesives used herein preferably have a viscosity of from greater than 2 to about 3000 centipoise and more preferably from greater than 2 to about 100 centipoise at 20° C. It is contemplated, however, that pastes and gels having viscosities of up to about 50,000 centipoise at 20° C. can also be employed and will make for easier skin application. Fumed silica can be used to achieve a viscosity between 1500–50,000.

The specific viscosity of the formulation depends on the amount and degree of partially polymerized cyanoacrylate adhesive employed as well as additives which are employed in the formulation to enhance or decrease viscosity. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety. Additives which can be incorporated into the formulation enhance its viscosity include polymers such as polymethyl methacrylates (PMMA) and polymerized cyanoacrylates as disclosed in U.S. Pat. Nos. 3,654,239 and 4,038,345 both of which are incorporated herein by reference in their entirety.

Monomeric forms of cyanoacrylate adhesives are often preferred where application is to be made to a large surface area. This preference results from the fact that these forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

For purposes of this invention, monomeric or partially polymerized n-butyl-2-cyanoacrylate or iso-butyl-2-cyanoacrylate is a particularly preferred adhesive and is capable of effectively bonding human skin tissue without causing histoxicity or cytotoxicity.

Upon contact with skin moisture and tissue protein, the cyanoacrylate adhesives will polymerize or, in the case of partially polymerized cyanoacrylate adhesives, will further polymerize, at ambient conditions (skin temperature) over about 10 to 60 seconds to provide a solid layer which forms over and strongly adheres to the surface of the skin. The resulting adhesive polymer layer or coating is flexible and waterproof thereby forming a protective layer which increases underlying skin integrity and reduces irritation to the surface skin area arising from shearing forces, moisture, friction, etc. In addition, the protective layer is an effective barrier against exposure to microorganisms, acids, caustics and enzymes and other deleterious materials present in human waste. (These harmful substances are collectively referred to as "human discharge" or "discharge" and includes urine and fecal wastes as well as other fluid components which may be incorporated therein, e.g., blood and perspiration.) Thus the protective layer is particularly useful for individuals suffering from incontinence. In addition, for patients who use ostomy appliances, a protective layer can be applied on the skin surrounding the stoma (or other artificial passage for bodily elimination). The protective layer also serves to reduce maceration of the skin caused by the ostomy appliances.

It is contemplated that the inventive methods can be used by themselves or can be employed in conjunction with existing regimens for inhibiting infections. For instances, in the case of incontinence patients, prior to formation of the protective layer, the intact skin can be cleaned, dried, and a bacteriostat (preferably water based) can be applied to the skin as further means of preventing infection.

The cyanoacrylate adhesive can also be applied as a protective layer over medicament, e.g. cortisone that has been applied to the skin. Preferably, the medicament is water based. The protective layer will adhere to the skin and afford a water resistant barrier film over the medicament. In one embodiment, after the medicament has been applied over a wound, the cyanoacrylate adhesive can be applied over the medicament and at least a portion of the skin surface along the periphery of the wound (or medicament). It is preferable to extend the protective layer on the skin up to about 1 centimeters from the periphery of the medicament and more preferably at least 5 centimeters.

The cyanoacrylate adhesive is applied to provide an effectively thick coating over the human skin tissue prone to be exposed to human discharge in the case of incontinence. Generally, the cyanoacrylate adhesive provides an adhesive coating over the entire skin area prone to exposure which, when set, is waterproof and satisfactorily flexible and adherent to the tissue without peeling or cracking. As is apparent, the thickness of the adhesive coating should be sufficient to afford a barrier against the various microorganisms and chemicals found in the discharge. In a particularly preferred embodiment, the thickness of the adhesive coating is from about 0.1 millimeter to about 0.5 millimeter and even more preferably from about 0.1 millimeter to about 0.3 millimeter. Preferably, the adhesive coating has a thickness of less than about 0.5 millimeter (mm), and more preferably the coating has a thickness of less than about 0.3 mm. It is understood that the adhesive coating, for any application, can be as thick as desired, but within practical limitations that are readily determined by a person skilled in the art. Moreover, with the present invention successive layers of adhesive coatings can be formed, if desired.

The adhesive coating can be formed by applying at least about 0.02 ml of cyanoacrylate adhesive per square centimeter of skin and more preferably from about 0.02 to about 0.2 ml of cyanoacrylate adhesive per square centimeter of skin and even more preferably from about 0.02 to about 0.1 ml of cyanoacrylate adhesive per square centimeter of skin. As is apparent, the amount of cyanoacrylate adhesive applied depends on, among other things, the concentration of the monomers and/or partially polymerized prepolymers used, and thickness of the protective coating desired. When the concentration is low and/or a thick coating is desired, the amount of cyanoacrylate adhesive applied can reach 0.2 ml per square centimeter of skin or higher.

FORMULATIONS

The cyanoacrylate adhesive formulations employed herein generally comprise monomeric and/or partially polymerized compounds of formula I described above and are sometimes referred to herein as simply cyanoacrylate adhesives. These formulations are liquid in nature and, upon contact with surface skin proteins and moisture, will polymerize to provide a solid film or layer over the skin surface.

The formulations may additionally comprise one or more optional additives such as colorants, perfumes, anti-diffusion agents, plasticizers, modifying agents and stabilizers. In practice, each of these optional additives should be both miscible and compatible with the cyanoacrylate adhesive. Compatible additives are those that do not prevent the use of the cyanoacrylate adhesives for their intended use.

In general, colorants are added so that the polymerized film will contain a discrete and discernable color. Perfumes are added to provide a pleasant smell to the formulation. Stabilizers, such as sulfur dioxide, are added to minimize in situ polymerization in containers during storage. Each of these additives is conventional. For example, suitable stabilizers are disclosed in U.S. Pat. No. 4,650,826 the disclosure of which is incorporated herein by reference in its entirety. Plasticizers, such as dioctylphthalate (about 18%–about 25% by weight, preferably about 20% ) or tri(p-cresyl)phosphate, can also be added in order to enhance the flexibility of the resulting polymer layer. Suitable plasticizers are disclosed in U.S. Pat. Nos. 2,784,127, and 4,444,933 the disclosures of all of these patents are incorporated herein by reference in their entirety.

The amount of each of these optional additives employed in the cyanoacrylate adhesive is an amount necessary to achieve the desired effect.

The formulation is generally stored in an applicator for use in a single dose application or for use in repeated applications. Single dose applicators include those having breakable or removable seals that prevent moisture, including atmospheric moisture, from contacting the formulation and causing in situ polymerization.

For repeated and intermittent usage, minimal exposure to atmospheric moisture is required. This can be achieved by devices having very narrow outlets and low initial deadspace. One applicator for such repeated intermittent use is described in U.S. Pat. No. 4,958,748 which is incorporated herein by reference.

Another applicator comprises a conventional spray applicator wherein the cyanoacrylate adhesive is sprayed onto the surface skin area prone to exposure to human waste. The spray rate of the applicator can be controlled so that application of a metered quantity of adhesive per unit area of skin surface over a set period of time is controlled.

Still another applicator comprises a brush or solid paddle applicator wherein the cyanoacrylate adhesive is "painted" onto the surface skin area prone to skin breakdown.

A preferred applicator for repeated and intermittent usage is an applicator suitable for the non-sterile storage and metered dispersement of a cyanoacrylate adhesive after opening of the applicator wherein the applicator is characterized as having a resealable opening of no more than about 0.008 square inches (0.0516 square centimeters) so as to permit the metered dispersement of the adhesive from the applicator and which is capable of multiple administrations of the adhesive and is further characterized as having resealing means such as a cap which either tightly mates with the applicator or which screws onto the applicator.

Preferably, the opening of the applicator is about 0.0016 to about 0.003 square inches (about 0.0103 to about 0.0194 square centimeters).

In another preferred embodiment, the walls of the applicator are made of a pliable material, so that upon application of pressure onto the walls, the walls depress sufficiently to force the adhesive contained in the applicator through the opening. Preferably, the applicator is manufactured with its opening covered by a metal foil or other similar construction which closes this opening until the device is ready for use. The opening is then reinstated by use of a pin or similar device which punctures the covering.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions can be achieved without regard to the sterility of the formulation.

METHODOLOGY

With respect to individuals suffering from incontinence, the methods of this invention provide for the in situ formation of a polymeric layer of cyanoacrylate adhesive over skin areas likely to be exposed to human discharge and, accordingly, are prone to skin breakage which can further lead to infection. The methods of this invention involve application of the above-described formulations to surface skin areas, that are prone to be exposed to human discharge, under conditions suitable for polymerizing the adhesive so as to form a protective coating. In general, sufficient amounts of cyanoacrylate adhesive are employed to cover (i.e., coat) the entire area that is prone to exposure, such as around the buttocks and thighs. The coating is preferably extended by at least about 1 centimeter and preferably by at least about 5 centimeters beyond the area expected to be exposed. (A similar strategy is employed for patients using ostomy appliances. Specifically, the adhesive coating is formed on skin around the periphery of an artificial passage (e.g., stoma) where the ostomy appliance is positioned.)

The adhesive polymer coating should be maintained in a unbroken manner over the entire area prone to exposure. This can be assured by careful application of the adhesive onto the skin. However, in a preferred embodiment, after the initial layer of adhesive has cured to provide for an adhesive polymer coating, a second, preferably thinner, layer is applied over the adhesive polymer coating. Additional amounts of cyanoacrylate adhesive can be applied as needed to maintain an unbroken protective covering over the surface skin areas.

Sufficient cyanoacrylate adhesive is preferably employed to form a coating of less than about 0.5 mm thick and more preferably at least about 0.1 mm thick. Such coatings can be formed by applying at least about 0.02 ml of cyanoacrylate adhesive per square centimeter of skin surface area.

The amount of cyanoacrylate adhesive applied onto the skin surface area can be controlled by the amount of adhesive packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive in a controlled dropwise manner. Other methods for the controlled dispersement of the cyanoacrylate adhesive are as described above including, by way of example, a conventional spray applicator, a brush or solid paddle applicator, and the like.

Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of an adhesive coating.

In general, the particular length of time required for polymerization will vary depending on factors such as the amount of adhesive applied, the temperature of the skin, the moisture content of the skin, the surface area of skin, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a coating while minimizing any action to prevent the adhesive from being dislodged from that portion of the skin where it was applied or to adhere to unintended objects. Excess adhesive polymer can be removed with acetone (nail polish remover) which can be readily conducted except in the case where the adhesive polymer binds to a sensitive skin part (e.g., the eye lids) where it should be removed by a health care professional.

After the adhesive coating has formed, the coating strongly adheres to the skin, is flexible and waterproof, thereby forming a protective coating which enhances the integrity of the underlying skin and protects the skin from exposure to human waste. Accordingly, the coating inhibits skin breakdown in the incontinent patient because the intact skin no longer is exposed to the human waste and because skin breakage is inhibited, subsequent infection of the broken skin is also inhibited. Furthermore, the protective coating also significantly reduces the amount of frictional stress the skin is subject to.

In general, the coating will adhere to the skin for a period of more than 24 hours and preferably for about at least 2–4 days after which time it sloughs off. Additional applications can be made if desired.

Because the cyanoacrylate adhesive polymer coating is waterproof and will not wash off, the patient is not prevented from bathing and other activities involving exposure to water during the period the adhesive layer protects this skin area.

The following examples illustrate certain embodiments of the invention but is not meant to limit the scope of the claims in any way.

EXAMPLES

Example 1

A cyanoacrylate adhesive formulation is prepared in monomeric form using n-butyl α-cyanoacrylate about 20% by weight dioctylphthlate and about 200 ppm $SO_2$. The formulation also contains a blue colorant to readily ascertain where it has been applied. The formulation is applied onto the buttocks/coccyx area in an amount of 0.1 milliliter per square centimeter of treated skin using a gloved finger and, after application, the skin is maintained at ambient condition until a polymer coating forms in about 30 to 120 seconds.

After the application of the cyanoacrylate adhesive layer on the skin has formed the polymer coating will protect the skin from feces and urine, while allowing the patient to wear a diaper-like garment commonly worn by patients with incontinence.

Example 2

The same formulation as described in Example 1 is applied under female breasts, and allowed to form a polymer coating. The flexible, waterproof coating prevents sweat sores from developing.

Example 3

The same formulation of Example 1 can be applied to the skin surface around the stoma (i.e. to the small intestines) to help protect the skin area from irritation by digestive juices, urine, or adhesives from the stoma bag (which is usually made of plastic).

From the foregoing description, various modifications and changes in the composition and method will occur to those skilled in the art. All such modifications coming within the scope of the appended claims are intended to be included therein.

What is claimed is:

1. A method for shielding a patient's skin from urine or fecal wastes caused by incontinence, which method comprises:

applying to a surface skin area which comes in contact with such urine or fecal wastes a sufficient amount of a cyanoacrylate adhesive to cover said area from said urine and/or fecal wastes; and polymerizing the cyanoacrylate adhesive so as to form a flexible, waterproof, adhesive polymer coating which adheres to the area where the adhesive was applied, wherein the cyanoacrylate, in monomeric form, is represented by formula I:

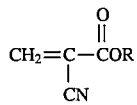

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

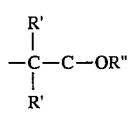

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

2. A method according to claim 1 wherein R is alkyl of from 2 to 8 carbon atoms.

3. A method according to claim 2 wherein R is butyl, pentyl or octyl.

4. A method according to claim 3 wherein R is n-butyl or isobutyl.

5. A method according to claim 1 wherein said adhesive is applied in an amount of at least 0.02 ml of cyanoacrylate adhesive per square centimeter of skin which is to be covered.

6. A method according to claim 5 wherein the cyanoacrylate adhesive is applied in an amount of from about 0.02 ml to about 0.2 ml per square centimeter of skin.

7. A method according to claim 6 wherein the cyanoacrylate adhesive is applied in an amount of from about 0.02 ml to about 0.1 ml per square centimeter of skin.

8. A method according to claim 1 wherein the cyanoacrylate adhesive has a viscosity of from greater than 2 to about 3000 centipoise at 20° C.

9. A method according to claim 8 wherein the cyanoacrylate adhesive has a viscosity of from greater than 2 to about 100 centipoise at 20° C.

10. A method according to claim 1 wherein the cyanoacrylate adhesive is applied from a single use applicator.

11. A method according to claim 1 wherein, prior to applying the cyanoacrylate adhesive onto the surface skin area, the method comprises of applying a bacteriostat onto the surface skin area.

12. A method for providing a protective covering over a medicament on a patient, which method comprises:

applying a medicament onto the skin:

applying onto said medicament and onto surface skin along the periphery of said medicament, a sufficient amount of a cyanoacrylate adhesive so as to cover said medicament and surface skin; and polymerizing the cyanoacrylate adhesive so as to form a flexible, waterproof, adhesive polymer coating which adheres to the surface skin where the adhesive was applied, wherein the cyanoacrylate, in monomeric form, is represented by formula I:

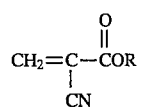

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

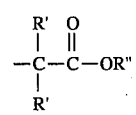

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

13. A method according to claim 12 wherein R is alkyl of from 2 to 8 carbon atoms.

14. A method according to claim 13 wherein R is butyl, pentyl or octyl.

15. A method according to claim 14 wherein R is n-butyl or isobutyl.

16. A method for providing a protective covering on skin along the periphery of a patient's stoma which method comprises:

applying onto said skin along the periphery of the stoma a sufficient amount of a cyanoacrylate adhesive so as to cover said skin; and polymerizing the cyanoacrylate adhesive so as to form a flexible, waterproof, adhesive polymer coating which adheres to the skin surface where the adhesive was applied, wherein the cyanoacrylate, in monomerie form, is represented by formula I:

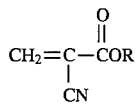
I.

where R is selected frown the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl, and a substituent of the formula:

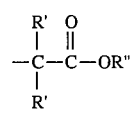
II.

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

17. A method according to claim 16 wherein R is alkyl of from 2 to 8 carbon atoms.

18. A method according to claim 17 wherein R is butyl, pentyl or octyl.

19. A method according to claim 18 wherein R is n-butyl or iso-butyl.

* * * * *